US00PP37178P2

(12) United States Plant Patent
Jimenez

(10) Patent No.: US PP37,178 P2
(45) Date of Patent: Dec. 23, 2025

(54) ***ARISTERIA* PLANT NAMED 'D GREY MOON'**

(50) Latin Name: *Aristeria beguinii*
Varietal Denomination: D GREY MOON

(71) Applicant: Deltacactus S.L., Amposta (ES)

(72) Inventor: Javier Andres Jimenez, Amposta (ES)

(73) Assignee: DeltaCactus S.L. (ES)

( * ) Notice: Subject to any disclaimer, the term of this patent is extended or adjusted under 35 U.S.C. 154(b) by 0 days.

(21) Appl. No.: 19/195,206

(22) Filed: Apr. 30, 2025

(51) Int. Cl.
*A01H 6/00* (2018.01)
*A01H 5/12* (2018.01)

(52) U.S. Cl.
USPC ..... Plt./373

(58) Field of Classification Search
USPC ..... Plt./373
CPC ..... A01H 6/00; A01H 5/12
See application file for complete search history.

*Primary Examiner* — Keith O. Robinson

(57) ABSTRACT

A new and distinct cultivar of *Aristeria* plant named 'D GREY MOON' is disclosed, characterized by an upright and uniform rosette shape. Foliage is uniquely dark greyed-green and densely covered with greyed-green lenticel dots. The new variety is an *Aristeria*, typically produced as an ornamental plant.

2 Drawing Sheets

Figure 1:
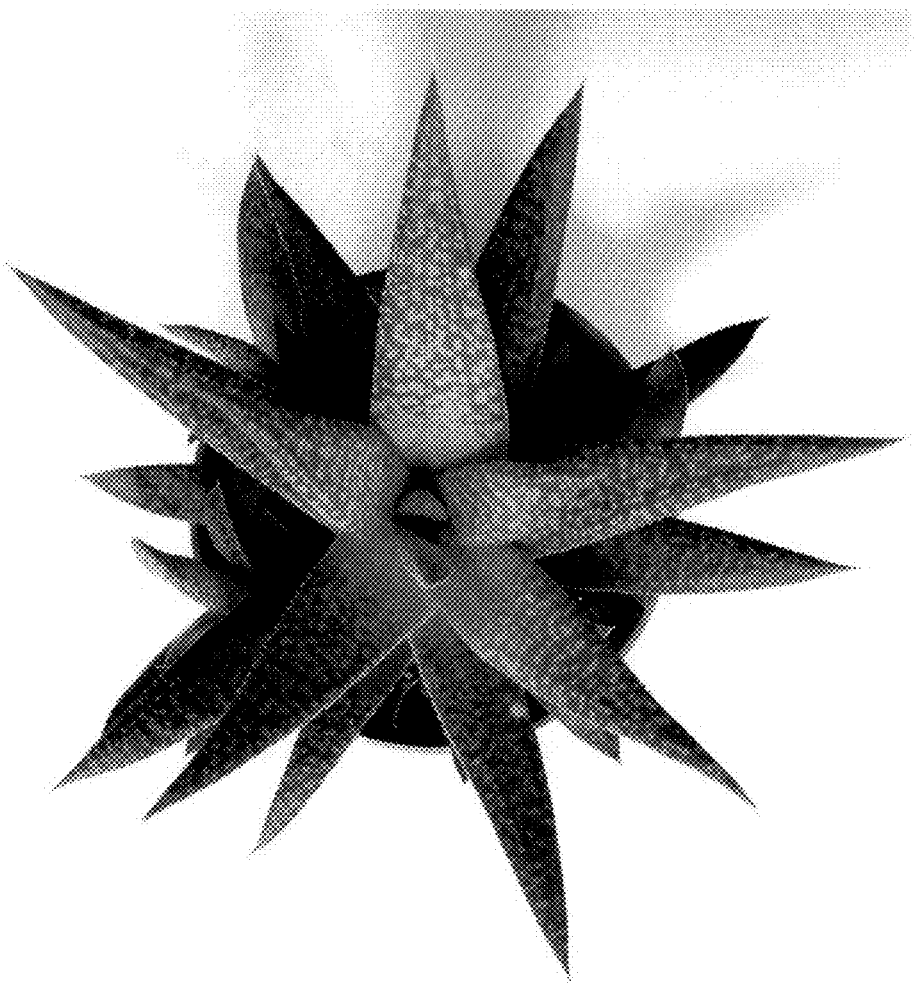

Latin name of the genus and species: *Aristeria beguinii.* Cultivar denomination: 'D GREY MOON'.

BACKGROUND OF THE INVENTION

The new cultivar is a product of a planned breeding program by the inventor, to produce distinct and better performing cultivars. The seed parent is the inventor's own hybrid *Gasteria carinata* #1018, unpatented. The pollen parent is the inventor's own hybrid, *Aristaloe aristata* #2001, unpatented. The crossing resulting in the new cultivar was made in 2019 at a nursery in Amposta, Spain. 'D GREY MOON' was found and selected by the inventor in March 2021 at the same location in Amposta, Spain.

Asexual reproduction of the new cultivar 'D GREY MOON' was first performed in Amposta, Spain in March 2021, by vegetative cuttings. 'D GREY MOON' has since produced several generations and has shown that the unique features of this cultivar are stable and reproduced true to type.

SUMMARY OF THE INVENTION

The cultivar 'D GREY MOON' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'D GREY MOON.' These characteristics in combination distinguish 'D GREY MOON' as a new and distinct *Aristeria* cultivar:

1. Dark greyed-green foliage color.
2. Upright and uniform rosette shape.

PARENTAL COMPARISONS

Plants of the new cultivar 'D GREY MOON' are similar to the seed parent in most horticultural characteristics. However, plants of the new cultivar differ in the following:

1. Plants of the new cultivar are rosette-like, having a radial symmetry, while plants of the seed parent are not rosette-shaped, but have a one axis symmetry.

Plants of the new cultivar 'D GREY MOON' are similar to the pollen parent in most horticultural characteristics. However, plants of the new cultivar differ in the following:

1. Leaf color of the new cultivar is grey-green, while the leaf color of the pollen parent is deep green.
2. Leaves of the new cultivar are much thicker than leaves of the pollen parent.

COMMERCIAL COMPARISONS

'D GREY MOON' can be compared to the commercial cultivar *Gasteraloe* 'D Delta', U.S. Plant Pat. No. 30,905. The two cultivars are similar in most horticultural characteristics; however, the new cultivar differs in the following:

1. Leaf color of the new cultivar is grey-green, while the leaf color of this comparator is green.
2. Leaves of the new cultivar are thicker and more upright than leaves of this comparator.

'D GREY MOON' can be compared to the commercial cultivar *Gasteraloe* 'WT01', U.S. Plant Pat. No. 22,012. The two cultivars are similar in most horticultural characteristics; however, the new cultivar differs in the following:

1. Leaf color of the new cultivar is grey-green, while the leaf color of this comparator is green.
2. Leaves of the new cultivar are thicker than leaves of this comparator.

BRIEF DESCRIPTION OF THE PHOTOGRAPHS

The accompanying photograph in FIG. 1 illustrates in full color a typical plant of 'D GREY MOON' grown in a greenhouse in Amposta, Spain. This plant is approximately 50 weeks old, shown in an 11 cm container.

Figure 2:
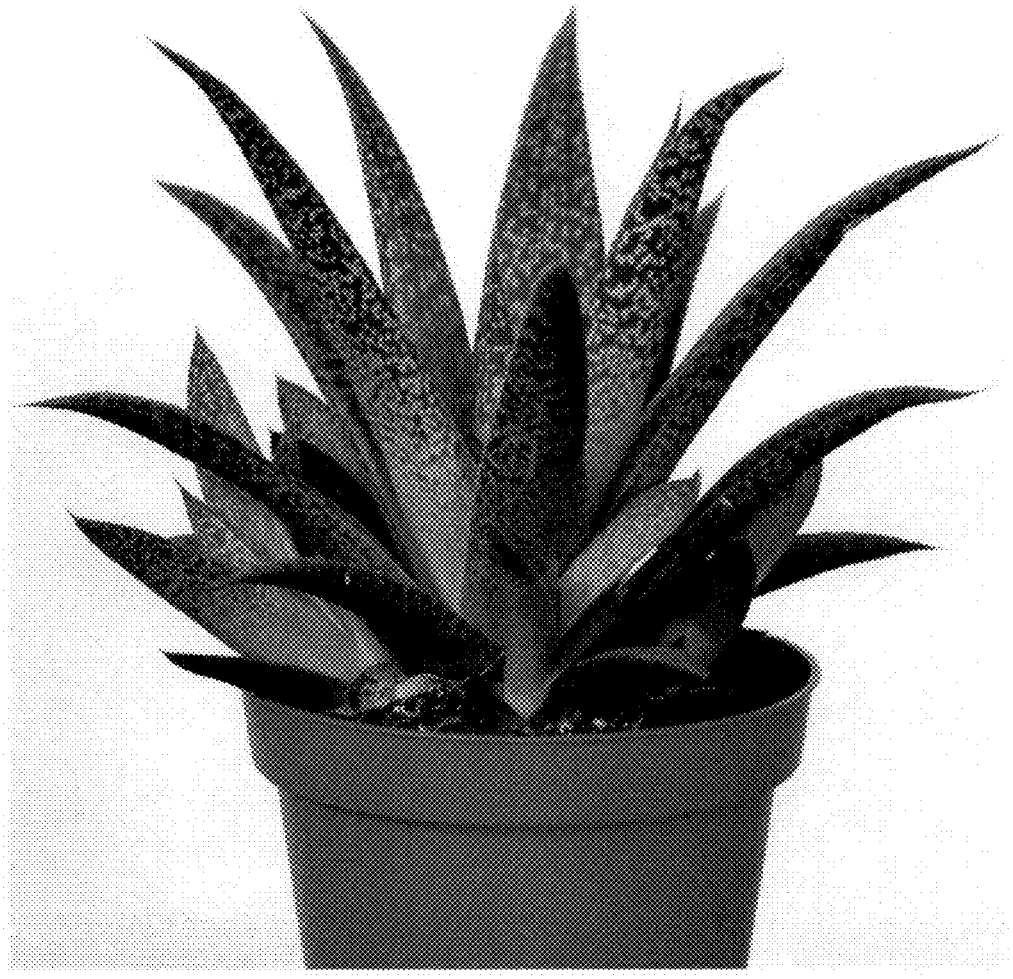

FIG. 2 illustrates a side-view of the same plant.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Color Chart, 2015 edition, except where general terms of ordinary dictionary significance are used. The following observations and measurements describe 'D GREY MOON' plants in a glass greenhouse in Amposta, Spain. Temperatures ranged from 18° C. to 20° C. during the day, and 15° C. to 18° C. during the night. No artificial light, photoperiodic treatments or chemical treatments were given to the plants. Measurements and numerical values represent averages of typical plant types.

Botanical classification: *Aristeria beguinii* 'D GREY MOON'.

Age of the plant described: 50 weeks.

PROPAGATION

Time to initiate roots: 14 days in summer; 21 days in winter at 20° C.

Time to produce rooted cutting: 80 days in summer; 90 days in winter at 20° C.

Root description: Fibrous, thick, moderately dense and freely-branching. White in color with yellow tips, not accurately measured with The R.H.S. Chart.

Propagation method: Vegetative cuttings.

PLANT

Plant type: Tender succulent perennial.

Plant shape: Flattened globular.

Growth habit: Basal rosette. One central rosette surrounded by an average of 9 secondary rosettes.

Container size: 11 cm pot.

Height: Average 13.6 cm; no flowering observed.

Plant spread: Average 16.8 cm.

Growth rate: Low to moderate.

Branching characteristics: Leaves in basal rosettes; 1 basal rosette per plant.

FOLIAGE

Leaf:

*Arrangement*.—Rosette.

*Quantity*.—Average 20 leaves per rosette.

*Average length*.—12.1 cm.

*Average width*.—2.4 cm.

*Thickness*.—1.1 cm.

*Shape of blade*.—Lanceolate, succulent.

*Whole leaf aspect*.—Very slightly concave.

*Apex*.—Narrow apiculate with a soft mucronate tip.

*Base*.—Broad cuneate.

*Margin*.—Finely serrate-dentate, average length and height of teeth: 0.3 mm, colored RHS Greyed-Green 190D.

*Texture of top surface*.—Densely pustulate, placed randomly on lamina, average width: 0.1 cm, average height: 0.3 mm and less, colored RHS Greyed-Green 191B.

*Texture of bottom surface*.—Densely pustulate, placed randomly on lamina, as well as arranged in axial lines. Average diameter 1.0 mm, average height: 0.1 mm, slightly taller, 0.3 mm towards distal end of lamina. Colored RHS Greyed-Green 191B and 191C.

*Pubescence*.—None.

*Rugosity*.—Both sides non-rugose.

*Luster*.—Upper side: Matte to very slightly glossy. Under side: Matte to very slightly glossy.

*Color*.—Young foliage upper side: RHS Yellow-Green 144A, fading to 152D towards base. Young foliage under side: RHS Green 143B; fading to Yellow-Green 152D towards base. Mature foliage upper side: RHS Yellow-Green 147A; fading to Yellow-Green 147B and 147C towards base. Base Greyed-White 156C and 156D. Mature foliage under side: Yellow-Green 147A, fading lighter towards the base; 147B and 147C. Base greyed-white; 156C and 156D. Lamina densely pustulate, placed randomly on lamina, as well as loosely arranged in axial lines, average diameter: 1.0 mm, average height: less than 0.1 mm, slightly higher towards distal end of lamina: 0.3 mm colored greyed-green; 191B and 191C.

*Venation*.—Pattern: Parallel. Color, upper side: Indistinguishable from leaf blade, Yellow-Green 147A. Color, under side: Indistinguishable from leaf blade, Yellow-Green 147A.

FLOWER

Flowering not observed to date.

REPRODUCTIVE ORGANS

Not observed to date.

OTHER CHARACTERISTICS

Seeds and fruits: Not observed to date.

Temperature tolerance: USDA Zones 10 through 12.

Tolerance to wind and rain: Low tolerance to rain; high tolerance to wind.

Disease/pest resistance: Neither resistance nor susceptibility to normal diseases and pests of *Aristeria* has been observed. Typical insect pests include mealybugs (*Pseudococcidae* spp.), spider mites (*Tetranychidae* spp.) and scale insects (*Hemiptera* spp.). Typical diseases are fungal, *Anthracnose, Cercospora* or *Alternaria*.

What is claimed is:

1. A new and distinct cultivar of *Aristeria* plant named 'D Grey Moon' as herein illustrated and described.

* * * * *